(12) United States Patent
Makino (10) Patent No.: US 12,347,070 B2
(45) Date of Patent: Jul. 1, 2025

(54) PROCESSOR FOR ELECTRONIC ENDOSCOPE AND ELECTRONIC ENDOSCOPIC SYSTEM

(71) Applicant: HOYA CORPORATION, Tokyo (JP)

(72) Inventor: Takao Makino, Tokyo (JP)

(73) Assignee: HOYA CORPORATION, Tokyo (JP)

(*) Notice: Subject to any disclaimer, the term of this patent is extended or adjusted under 35 U.S.C. 154(b) by 65 days.

(21) Appl. No.: 18/274,914

(22) PCT Filed: Mar. 11, 2022

(86) PCT No.: PCT/JP2022/010802
§ 371 (c)(1),
(2) Date: Jul. 28, 2023

(87) PCT Pub. No.: WO2022/209732
PCT Pub. Date: Oct. 6, 2022

(65) Prior Publication Data
US 2024/0087090 A1    Mar. 14, 2024

(30) Foreign Application Priority Data
Mar. 31, 2021   (JP) .................................. 2021-060673

(51) Int. Cl.
*G06T 7/00*     (2017.01)
*A61B 1/00*     (2006.01)
(Continued)

(52) U.S. Cl.
CPC .......... *G06T 5/00* (2013.01); *A61B 1/000095* (2022.02); *G06T 7/90* (2017.01);
(Continued)

(58) Field of Classification Search
CPC ... G06T 5/00; G06T 7/90; G06T 2207/10024; G06T 2207/10068; G06T 2207/30096;
(Continued)

(56) References Cited

U.S. PATENT DOCUMENTS 6,293,911 B1 *  9/2001  Imaizumi ......... A61B 1/000094
                                                600/178
6,527,708 B1 *  3/2003  Nakamura ........... A61B 1/0005
                                                600/109
(Continued)

FOREIGN PATENT DOCUMENTS

EP      3 430 969 A1    1/2019
JP      3842995 B2      8/2006
(Continued)

OTHER PUBLICATIONS

European Search Report issued in EPO Patent Application No. 22779953.3, dated Oct. 15, 2024.
(Continued)

*Primary Examiner* — Frank F Huang
(74) *Attorney, Agent, or Firm* — GREENBLUM & BERNSTEIN, P.L.C.

(57) ABSTRACT

An aspect of the present invention is a processor for an electronic endoscope that acquires a captured image of a living tissue and performs enhancement processing. The processor includes: a region detection unit configured to detect an enhancement processing target region in the captured image from pixel information of the captured image of the living tissue; and an enhancement processing unit configured to perform enhancement processing on the enhancement processing target region detected by the region detection unit. The region detection unit detects the enhancement processing target region based on a difference in signal level between a pixel of interest in the captured image and a pixel surrounding the pixel of interest, and the enhancement processing unit performs enhancement processing on the enhancement processing target region such that enhancement is weakened as the difference in signal level is larger and enhancement is strengthened as luminance is higher.

9 Claims, 7 Drawing Sheets

(51) Int. Cl.
*G06T 5/00* (2006.01)
*G06T 7/90* (2017.01)

(52) U.S. Cl.
CPC .............. *G06T 2207/10024* (2013.01); *G06T 2207/10068* (2013.01); *G06T 2207/30096* (2013.01); *G06T 2207/30101* (2013.01)

(58) Field of Classification Search
CPC ............ G06T 2207/30101; G06T 5/20; A61B 1/000095; A61B 1/000094
See application file for complete search history.

(56) References Cited

U.S. PATENT DOCUMENTS

| | | | |
|---|---|---|---|
| 10,602,918 B2* | 3/2020 | King | A61B 1/0607 |
| 10,646,110 B2* | 5/2020 | Fukuda | A61B 1/000095 |
| 2002/0196335 A1 | 12/2002 | Ozawa | |
| 2003/0076412 A1 | 4/2003 | Ozawa | |
| 2003/0231791 A1* | 12/2003 | Torre-Bueno | G06T 5/50 |
| | | | 382/133 |
| 2004/0245350 A1* | 12/2004 | Zeng | A61B 1/042 |
| | | | 236/77 |
| 2006/0256191 A1* | 11/2006 | Iketani | A61B 1/0005 |
| | | | 348/65 |
| 2009/0270678 A1* | 10/2009 | Scott | A61B 1/043 |
| | | | 600/109 |
| 2010/0195904 A1 | 8/2010 | Tsuruoka | |
| 2012/0013773 A1* | 1/2012 | Yoshino | G06T 7/32 |
| | | | 348/241 |
| 2012/0183198 A1* | 7/2012 | Zahniser | G06V 20/693 |
| | | | 382/133 |
| 2014/0028699 A1* | 1/2014 | Kurtz | H04N 9/67 |
| | | | 345/590 |
| 2014/0241645 A1 | 8/2014 | Esaki | |
| 2014/0378843 A1* | 12/2014 | Valdes | A61B 1/063 |
| | | | 600/476 |
| 2015/0287192 A1 | 10/2015 | Sasaki | |
| 2016/0078625 A1 | 3/2016 | Tajbaksh et al. | |
| 2016/0284061 A1 | 9/2016 | Kano | |
| 2017/0017069 A1* | 1/2017 | Siegel | A61B 5/0075 |
| 2018/0119141 A1* | 5/2018 | Chen | G01N 33/5014 |
| 2020/0258217 A1 | 8/2020 | Makino | |
| 2020/0345205 A1 | 11/2020 | Makino et al. | |

FOREIGN PATENT DOCUMENTS

| | | |
|---|---|---|
| JP | 3869698 B2 | 10/2006 |
| JP | 3976950 B2 | 6/2007 |
| JP | 2014-138691 A | 7/2014 |
| JP | 2014-164661 A | 9/2014 |
| JP | 2016-184888 A | 10/2016 |
| WO | 2019/087895 A1 | 9/2019 |
| WO | 2019/088259 A1 | 9/2019 |

OTHER PUBLICATIONS

International Search Report issued in International Bureau of WIPO Patent Application No. PCT/JP2022/010802, dated May 31, 2022, along with an English translation thereof.

* cited by examiner

PROCESSOR FOR ELECTRONIC ENDOSCOPE AND ELECTRONIC ENDOSCOPIC SYSTEM

TECHNICAL FIELD

The present invention relates to a processor for an electronic endoscope that acquires a captured image of a living tissue and performs enhancement processing on the captured image, and an electronic endoscope system.

BACKGROUND ART

An electronic endoscope device is used for observation and treatment of a living tissue inside a human body. Enhancement processing of surface irregularities, which makes a concave portion noticeable such that the surface irregularities of the living tissue can be observed from a captured image obtained by imaging the living tissue by using the electronic endoscope device, is performed on the captured image, and the resultant is displayed on a display. Since a lesion of the living tissue has more irregularities on the surface than a healthy portion, the display of the captured image with enhanced surface irregularities is useful to find the lesion.

There is known an electronic endoscope device that can reliably enhance a concave portion on a surface of a living tissue and, as a result, can reliably diagnose even a slight lesion without oversight (Refer to JP 3869698 B1).

This electronic endoscope device generates a video color signal based on one frame of color pixel signals read from a solid-state image sensor provided at a distal end of a scope. The electronic endoscope device includes: a comparison means for comparing a signal level value of a color pixel signal corresponding to a specific pixel included in one frame of color pixel signals with signal level values of color pixel signals corresponding to all adjacent surrounding pixels adjacent to the surrounding of the specific pixel in a predetermined pixel array direction; and a color balance change means for changing color balance of a video color signal by changing the signal level value of the color pixel signal corresponding to the specific pixel according to a comparison result obtained by the comparing means.

SUMMARY OF INVENTION

Technical Problem

The electronic endoscope device extracts a concave portion of surface irregularities of a living tissue with a mucous membrane by performing comparison with the signal level values of the color pixel signals corresponding to all the adjacent surrounding pixels adjacent to the surrounding of the specific pixel in the predetermined pixel array direction, and further, reduces a signal level value of a specific color component of a pixel of the extracted concave portion to create an image in which a color of a portion corresponding to the concave portion has been changed as an image with the enhanced surface irregularities.

In the electronic endoscope device, when extracting the concave portion, the comparison is performed with the signal level values of the color pixel signals corresponding to all the adjacent surrounding pixels adjacent to the surrounding of the specific pixel in the specific pixel array direction, and thus the extraction of the concave portion depends on a signal level difference between the pixel signals. That is, since the signal level between the concave portion and a region around the concave portion increases as the concave portion is deeper, the enhancement is strengthened as the concave portion is deeper. However, in this enhancement processing method, a portion that is not the concave portion and has a large signal level difference from the vicinity, such as a blood vessel or a highlight portion, is also greatly enhanced, and the concave portion may not be capable of being made noticeable.

Therefore, an object of the present invention is to provide a processor for an electronic endoscope capable of effectively performing enhancement processing on a concave portion as compared with the related art when acquiring a captured image of the living tissue and performing the enhancement processing, and an electronic endoscope system.

Solution to Problem

An aspect of the present invention is a processor for an electronic endoscope that acquires a captured image of a living tissue and performs enhancement processing. The processor includes:
  a region detection unit configured to detect an enhancement processing target region in the captured image from pixel information of the captured image of the living tissue; and
  an enhancement processing unit configured to perform enhancement processing on the enhancement processing target region detected by the region detection unit.
  The region detection unit detects the enhancement processing target region based on a difference in signal level between a pixel of interest in the captured image and a pixel surrounding the pixel of interest, and
  the enhancement processing unit performs enhancement processing on the enhancement processing target region such that enhancement is weakened as the difference in signal level is larger and the enhancement is strengthened as luminance is higher.

The enhancement processing may be processing of correcting a pixel value of a pixel included in the enhancement processing target region based on a first coefficient for the difference in signal level and a second coefficient for intensity of the luminance.

The first coefficient and/or the second coefficient may be individually set for each of RGB components of the pixel included in the enhancement processing target region.

An input unit for setting or changing the first coefficient and the second coefficient may be further included.

The enhancement processing may be performed such that the enhancement is strengthened as a value of an R component and/or a value of a G component of the pixel included in the enhancement processing target region is larger.

In a case where a signal level value of the pixel of interest is smaller than the signal level values of two farthest pixels located on both sides farthest from the pixel of interest in any one of a plurality of pixel array directions in a region surrounded by a frame surrounding a region centered on the pixel of interest, the region detection unit may be configured to repeat candidate extraction processing of extracting the pixel of interest as a candidate for the enhancement processing target region while changing a size of the frame and to define the enhancement processing target region based on the pixel extracted as the candidate by changing the size of the frame.

Another aspect of the present invention is an electronic endoscope system including the processor for an electronic endoscope, and an electronic endoscope that is connected to the processor for an electronic endoscope and includes an image sensor configured to capture the living tissue.

Advantageous Effects of Invention

According to the processor for an electronic endoscope and the endoscope system described above, it is possible to effectively perform the enhancement processing on the concave portion as compared with the related art.

DESCRIPTION OF EMBODIMENTS

A processor of an electronic endoscope system according to the present embodiment detects a region of a concave portion of a living tissue, for example, as an enhancement processing target region to be subjected to enhancement processing in a captured image obtained by imaging the living tissue in the system. The region of the concave portion includes regions having various sizes. The enhancement processing target region is detected based on a difference in signal level between a pixel of interest and pixels surrounding the pixel of interest in the captured image. However, when the enhancement processing is performed more strongly as the difference is larger, a great enhancement is also performed on a portion that is not a concave portion and has a large signal level difference from the vicinity, such as a blood vessel and a highlight portion. Thus, the processor according to an embodiment is configured to perform enhancement processing on the enhancement processing target region such that the enhancement is weakened as the signal level difference is larger and the enhancement is strengthened as the luminance is higher. Therefore, the irregularities of the mucous membrane can be enhanced in the captured image, and the lesion can be more effectively noticed as in the case of pigmentation.

Hereinafter, the electronic endoscope system of the present embodiment will be described in detail with reference to the drawings.

Figure 1:
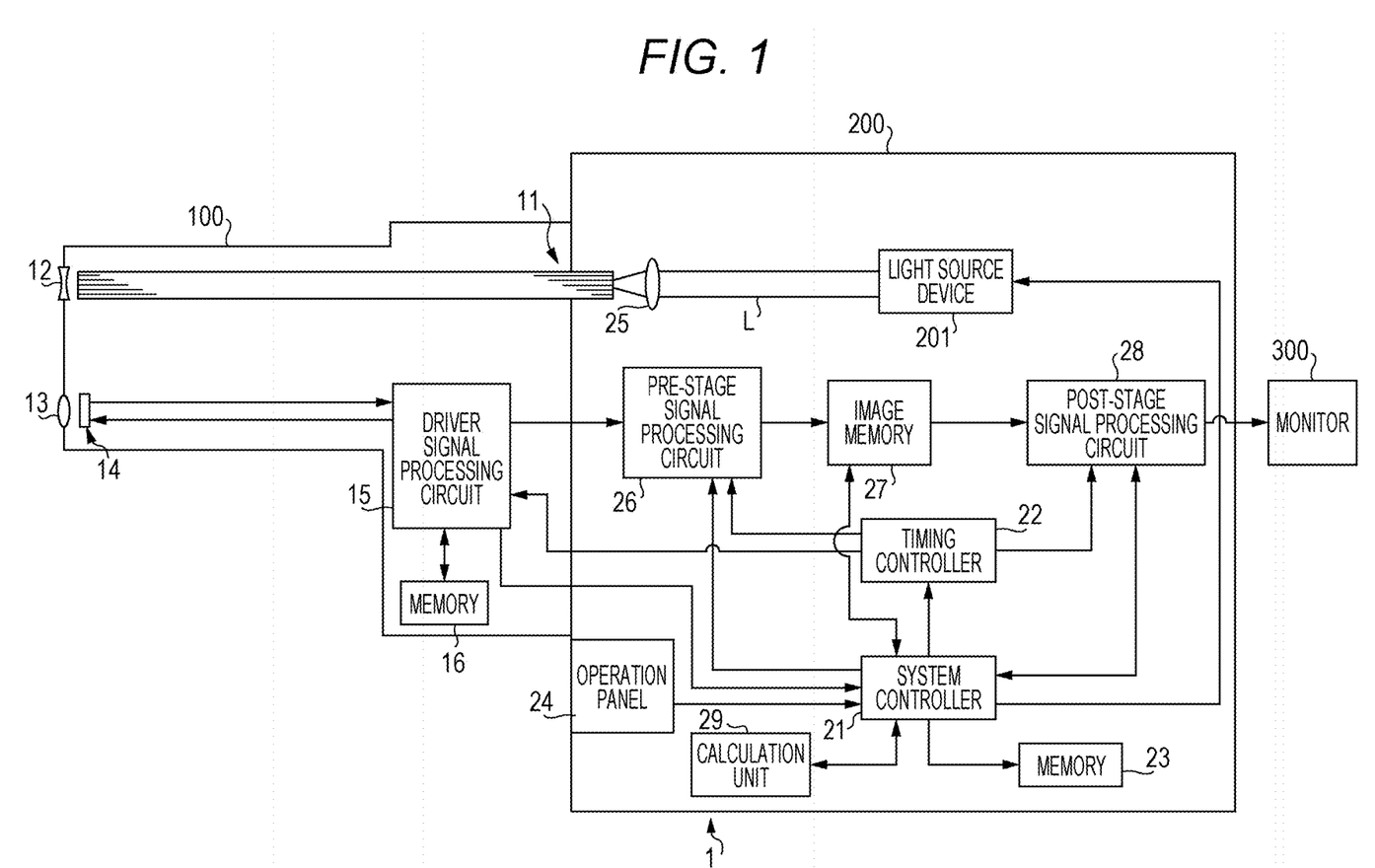
FIG. 1 is a block diagram illustrating an example of a configuration of an electronic endoscope system of an embodiment.

FIG. 1 is a block diagram illustrating an example of a configuration of an electronic endoscope system 1 of the present embodiment. As illustrated in FIG. 1, the electronic endoscope system 1 is a system specialized for medical use, and includes an electronic scope (endoscope) 100, a processor 200, and a monitor 300.

The processor 200 includes a system controller 21 and a timing controller 22. The system controller 21 executes various programs stored in a memory 23 and integrally controls the entire electronic endoscope system 1. Furthermore, the system controller 21 is connected to an operation panel 24. The system controller 21 changes operations of the electronic endoscope system 1 and a parameter for each of the operations in accordance with an operator's instruction input to the operation panel 24. The timing controller 22 outputs a clock pulse for adjusting an operation timing of each unit to each of circuits in the electronic endoscope system 1.

The processor 200 includes a light source device 201. The light source device 201 emits illumination light L for illuminating an object such as a living tissue in a body cavity. The illumination light L includes white light, pseudo white light, or special light. According to the embodiment, it is preferable that the light source device 201 selects one of a mode of constantly emitting the white light or the pseudo white light as the illumination light L and a mode of alternately emitting the white light or pseudo white light and the special light as the illumination light L, and emits the white light, the pseudo white light, or the special light based on the selected mode. The white light is light having a flat spectral intensity distribution in a visible light band, and the pseudo white light is light which is a mixture of light of a plurality of wavelength bands and has non-flat spectral intensity distribution. The special light is light of a narrow wavelength band, such as blue or green, in the visible light band. The light of the blue or green wavelength band is used at the time of enhancing a specific portion of the living tissue and observing the portion. The illumination light L emitted from the light source device 201 is condensed onto an incident end face of a Light Carrying Bundle (LCB) 11 by a condenser lens 25, and is incident into the LCB 11.

The illumination light L incident into the LCB 11 propagates through the LCB 11. The illumination light L propagating through the LCB 11 is emitted from an exit end face of the LCB 11 disposed at a distal end of the electronic scope 100, and is radiated to the object via a light distribution lens 12. Return light from the object illuminated with the illumination light L from the light distribution lens 12 forms an optical image on a light receiving surface of a solid-state image sensor 14 via an objective lens 13.

The solid-state image sensor 14 is a single-plate color charge coupled device (CCD) image sensor having a Bayer pixel arrangement. The solid-state image sensor 14 accumulates an optical image formed by each of pixels on the light receiving surface, as charge corresponding to the amount of light, and generates and outputs image signals of Red (R), Green (G), and Blue (B). Note that the solid-state image sensor 14 is not limited to a CCD image sensor, and may be replaced with a complementary metal oxide semiconductor (CMOS) image sensor or other types of imaging devices. Furthermore, the solid-state image sensor 14 may include a complementary color filter.

A driver signal processing circuit 15 is provided in a connection portion of the electronic scope 100. An image signal of the object is input to the driver signal processing circuit 15 from the solid-state image sensor 14 in a predetermined frame cycle. For example, the frame cycle is 1/30 seconds. The driver signal processing circuit 15 performs predetermined processing on the image signal input from the solid-state image sensor 14 and outputs the processed image signal to a pre-stage signal processing circuit 26 of the processor 200.

Furthermore, the driver signal processing circuit 15 accesses a memory 16 and reads information specific to the electronic scope 100. The information specific to the electronic scope 100 recorded in the memory 16 includes, for example, the number of pixels and sensitivity of the solid-state image sensor 14, an operable frame rate, and a model number. The driver signal processing circuit 15 outputs the specific information read from the memory 16 to the system controller 21. Examples of this specific information may include information unique to an element, such as the number of pixels of the solid-state image sensor 14 and the resolution of the solid-state image sensor 14, and information regarding an optical system, such as an angle of view, a focal length, and a depth of field.

The system controller 21 performs various calculation based on the information specific to the electronic scope 100 and generates a control signal. The system controller 21 controls the operation and timing of each circuit in the processor 200 by using the generated control signal so as to perform processing suitable for the electronic scope 100 connected to the processor 200.

The timing controller 22 supplies a clock pulse to the driver signal processing circuit 15 in accordance with timing control performed by the system controller 21. The driver signal processing circuit 15 performs driving control for the solid-state image sensor 14 at a timing synchronized with the frame rate of a video image processed by the processor 200 in accordance with the clock pulse supplied from the timing controller 22.

The pre-stage signal processing circuit 26 performs predetermined signal processing such as demosaic processing, matrix calculation, and Y/C separation on the image signal input from the driver signal processing circuit 15 in one frame cycle, and outputs the processed image signal to an image memory 27.

The image memory 27 buffers the image signal input from the pre-stage signal processing circuit 26 and outputs the image signal to a post-stage signal processing circuit 28 in accordance with the timing control performed by the timing controller 22.

The post-stage signal processing circuit 28 processes the image signal input from the image memory 27 to generate monitor display screen data, and converts the generated monitor display screen data into a predetermined video format signal. The converted video format signal is output to the monitor 300. With this processing, an image of the object is displayed on a display screen of the monitor 300.

Figure 2:
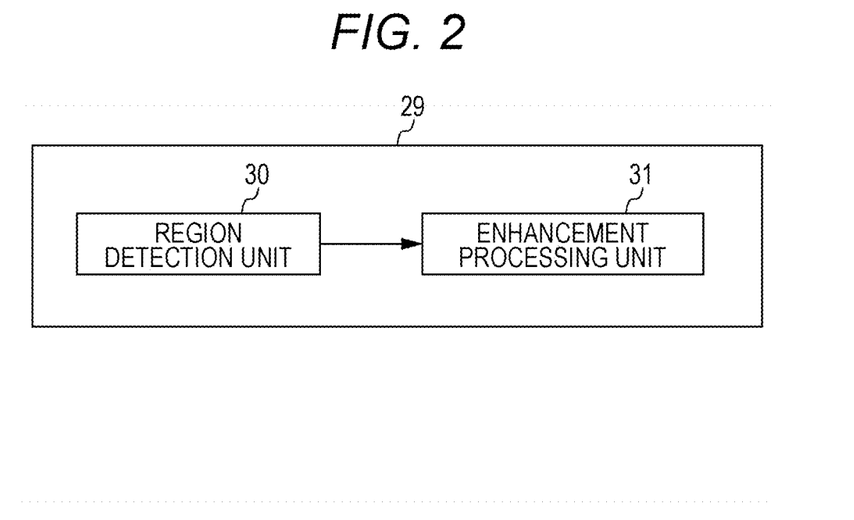
FIG. 2 is a block diagram illustrating an example of a configuration of a calculation unit illustrated in FIG. 1.

A calculation unit 29 is connected to the system controller 21. The calculation unit 29 is a unit that extracts a region having the concave portion of the living tissue as an enhancement processing target region of the captured image which is obtained by imaging the living tissue to be stored and called from the image memory 27 via the system controller 21, and performs enhancement processing on this enhancement processing target region. FIG. 2 is a block diagram illustrating an example of a configuration of the calculation unit 29. The calculation unit 29 includes a region detection unit 30 and an enhancement processing unit 31.

The region detection unit 30 is configured to detect an enhancement processing target region that is to be enhanced from information regarding pixels of the captured image of the living tissue. In a region detection processing, the region detection unit 30 uses a frame surrounding a region centered on a pixel of interest to be described below to perform a candidate extraction processing of extracting a candidate for an enhancement processing target region while repeatedly changing a size of the frame, and defines the enhancement processing target region based on pixels extracted as candidates. Here, the candidate extraction processing is processing of extracting a pixel of interest as a candidate for the enhancement processing target region in a case where a signal level value of the pixel of interest is smaller than signal level values of two farthest pixels located on both sides farthest from the pixel of interest in any one of a plurality of pixel array directions in a region surrounded by a frame surrounding the region with the pixel of interest as a center. Therefore, even when it is difficult to extract a candidate pixel in a frame of a certain size, a candidate pixel is extracted in a frame of another size in some cases. Details will be described later.

The enhancement processing unit 31 is configured to perform enhancement processing on the enhancement processing target region detected by the region detection unit 30. In the enhancement processing on the enhancement processing target region, the enhancement is weakened as the signal level difference is larger and the enhancement is strengthened as the luminance is higher. More specifically, the enhancement processing includes processing of correcting a pixel value of each pixel included in the enhancement processing target region based on a first coefficient for the signal level difference and a second coefficient for the luminance component.

For example, in a case where a pixel value before the enhancement processing is represented by Ii and a pixel value after the enhancement processing is represented by Ii', the enhancement processing unit 31 performs the enhancement processing in accordance with Equation (1) below with respect to a pixel of interest i of each color component of RGB included in the enhancement processing target region in an RGB color captured image.

$$Ii'=Ii \cdot (\alpha i - \beta i \cdot D + \gamma i \cdot Y) \qquad \text{Equation (1)}$$

In Equation (1), D is a difference value between the pixel value Ii of the pixel of interest i and an average value of the pixel values of surrounding pixels around the pixel of interest i, and means depth information corresponding to the depth of the concave portion. Y is luminance information in the pixel of interest i.

$\alpha i$ and $\beta i$ (examples of a first coefficient), and $\gamma i$ (an example of the second coefficient) are enhancement coefficients and positive values, respectively. $\alpha i$ is a base enhancement coefficient, and $\beta i$ and $\gamma i$ are enhancement coefficients for the depth information D and the luminance information Y, respectively. $\alpha i$, $\beta i$, and $\gamma i$ are values set in advance or values input and set from the operation panel 24. Each of $\alpha i$, $\beta i$, and $\gamma i$ may be a constant value regardless of a pixel position, or may be a value that varies according to a predetermined condition. Furthermore, $\alpha i$, $\beta i$, and $\gamma i$ may be different for each color component.

Here, the surrounding pixels around the pixel of interest i may be two farthest pixels that have been compared with the signal level value of the pixel of interest i when defining the above-described enhancement processing target region, may be eight adjacent pixels surrounding the pixel of interest i in an up-down direction, a left-right direction, an upper right-lower left direction, and an upper left-lower right direction, or may be eight farthest pixels farthest from the pixel of interest i in the up-down direction, the left-right direction, the upper right-lower left direction, and the upper left-lower right direction in the frame.

As indicated in parentheses on the right side of Equation (1), the enhancement processing on the pixel of interest i is performed such that the enhancement is suppressed as the value of the depth information D is larger, and the enhancement is performed as the value of the luminance information Y is larger. Since the enhancement is suppressed as the value of the depth information D is larger, it is possible to prevent a blood vessel or a highlight portion that is not a concave portion from being enhanced. However, when the enhancement is only suppressed as the value of the depth information D is larger, the enhancement on the concave portion present in the high luminance portion is also weakened. Therefore, since the enhancement is strengthened as the value of the luminance information Y is larger by γi, it is possible to enhance the concave portion without enhancing the blood vessel or the highlight portion.

Figure 3:
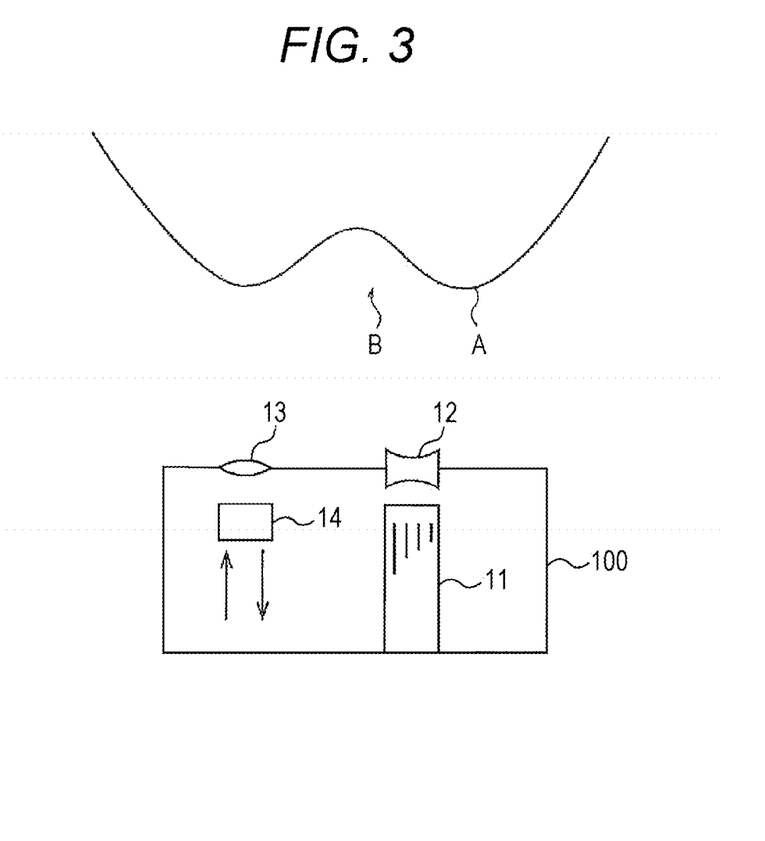
FIG. 3 is a diagram illustrating an example of imaging of a living tissue by an endoscope illustrated in FIG. 1.

FIG. 3 is a diagram illustrating an example of imaging of a living tissue A by the electronic scope (endoscope) 100. The living tissue A has a concave portion B that is recessed in the depth direction when viewed from the electronic scope 100. The electronic scope 100 images the living tissue A including the concave portion B.

Here, the size of the region (concave region) corresponding to the concave portion B in the captured image obtained changes depending on an imaging distance of the electronic scope 100 to the living tissue A.

That is, the width of the concave region may be the size of one pixel or the width of the concave region may exceed the size of one pixel. In consideration of the concave region of which the size changes depending on the imaging distance in this manner, the region detection unit 30 causes frames to have a plurality of sizes, the frames surrounding a region around a pixel of interest with the pixel of interest used at the time of performing the region detection processing as the center pixel.

Note that the calculation unit 29 may be a software module that is formed as a module when the system controller 21 activates a program stored in the memory 23, and may be a hardware module configured with a field-programmable gate array (FPGA).

Figure 4:
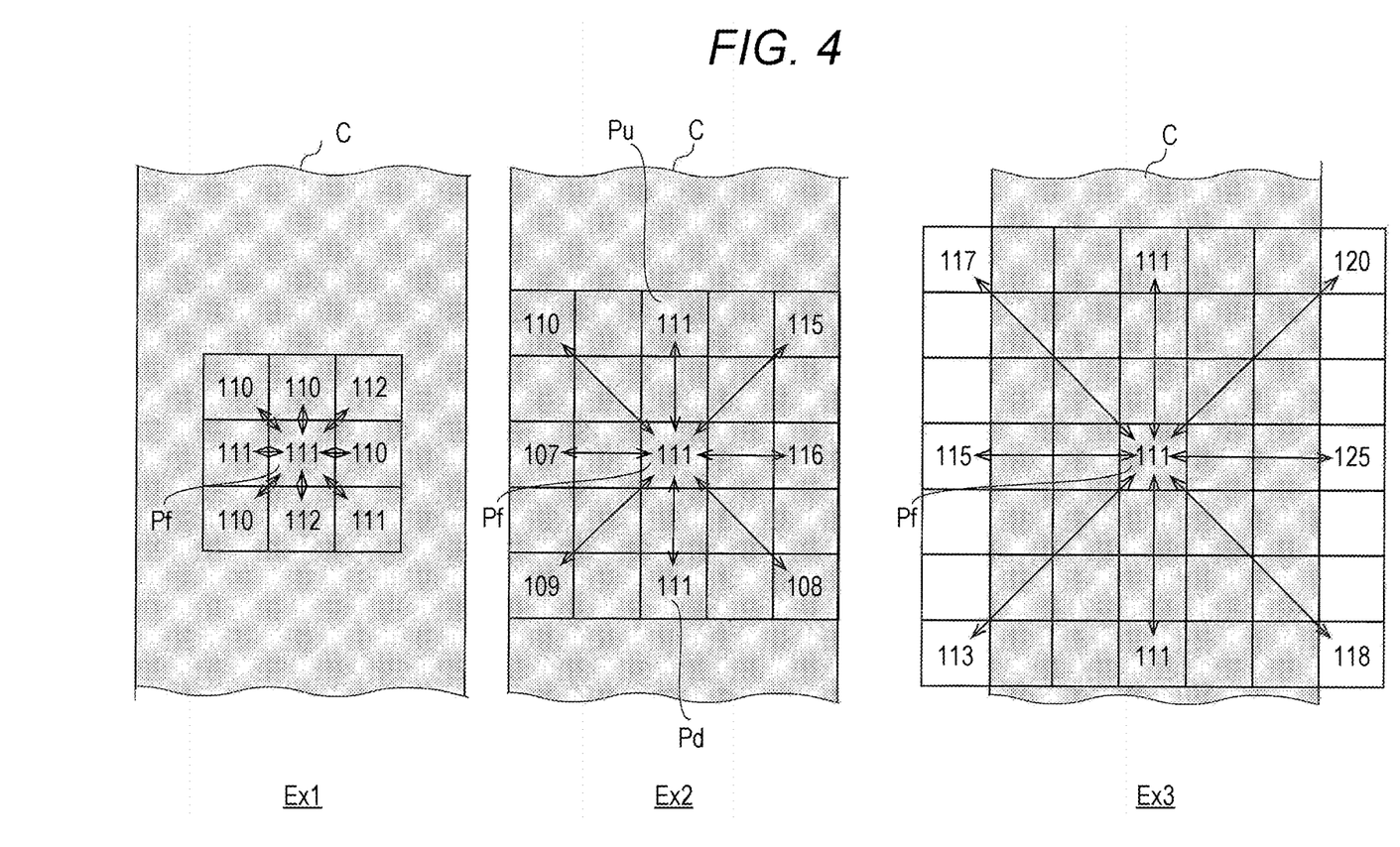
FIG. 4 is diagram illustrating examples of processing performed by a calculation unit of the present embodiment.

Ex1 to Ex3 of FIG. 4 are diagrams illustrating examples of processing performed by the region detection unit 30 of the calculation unit 29. For example, Ex1 to Ex3 of FIG. 4 illustrate a frame 33 of 3×3 pixels, a frame 55 of 5×5 pixels, and a frame 77 of 7×7 pixels, respectively. The frames 33, 55, and 77 are disposed such that each pixel at the center of the frame matches the pixel of interest in the captured image. Numerical values illustrated in the pixels of Ext and Ex3 in FIG. 4 are examples of signal level values of the pixels. The signal level value of the pixel of interest is 111.

For example, the region detection unit 30 extracts a pixel of interest Pf as a candidate for the enhancement processing target region in a case where a signal level value of the pixel of interest Pf is smaller than signal level values of two farthest pixels located on both sides farthest from the pixel of interest Pf in any of the up-down direction, the left-right direction, the upper right-lower left direction, and the upper left-lower right direction in a region surrounded by the frame 33 surrounding the region centered on the pixel of interest Pf of the captured image. In general, since the illumination light L does not reach the concave portion sufficiently at the time of imaging, and the return light of the illumination light L does not sufficiently reach the light receiving surface of the solid-state image sensor 14, the concave portion appears as a dark region in the captured image. Therefore, it is possible to extract a candidate for the region corresponding to the concave portion by examining whether or not the signal level value of the pixel of interest is smaller than the signal level value of any of the farthest pixels.

In a case where it is difficult to extract a candidate for the region corresponding to the concave portion in the frame 33, the same processing as the above-described processing is performed using the frame 55 instead of the frame 33. In this case, in the example illustrated in Ext of FIG. 4, two farthest pixels farthest from the pixel of interest Pf and located on both sides in the up-down direction are pixels Pu and Pd. In a case where it is also difficult to extract a candidate for the region corresponding to the concave portion in the frame 55, the same processing as the above-described processing is further performed using the frame 77 instead of the frame 55. In the example illustrated in Ext of FIG. 4, it is difficult to extract a candidate for the region corresponding to the concave portion. In the example illustrated Ex3 of FIG. 4, it is possible to extract a candidate for the region corresponding to the concave portion in the left-right direction, the upper right-lower left direction, and the upper left-lower right direction.

Note that there is a case where no farthest pixel exists in a frame when the image of interest is located at one of the upper, lower, left, and right ends of the captured image or is located in the vicinity of the captured image. In this case, the processing of extracting the candidate in any of the up-down direction, the left-right direction, the upper right-lower left direction, and the upper left-lower right direction is not performed.

The region detection unit 30 defines the enhancement processing target region based on the pixel extracted as the candidate by changing the size of the frame. For example, a pixel, in which the number of times the same pixel is set as a candidate in the pixel array directions of the left-right direction, the upper right-lower left direction, and the upper left-lower right direction is equal to or larger than a preset threshold count, is defined as the enhancement processing target region. In a case where the threshold count is one, all the pixels extracted as candidates are set as the enhancement processing target regions. In a case where the threshold count is two or more, a pixel, in which the number of times of setting is equal to or larger than the threshold count, is set as the enhancement processing target region among pixels extracted as candidates. As illustrated in Ex3 of FIG. 4, the pixel of interest Pf is extracted as the candidate three times since the signal level value of 111 of the pixel of interest Pf is smaller than signal level values (signal level values of 115 and 125, signal level values of 120 and 113, and signal level values of 117 and 118) of two farthest pixels located on both sides farthest from the pixel of interest Pf (the signal level value of 111) in the left-right direction, the upper right-lower left direction, and the upper left-lower right direction. Therefore, the pixel of interest Pf is set as the enhancement processing target region in the example illustrated in Ex3 of FIG. 4.

Figure 5:
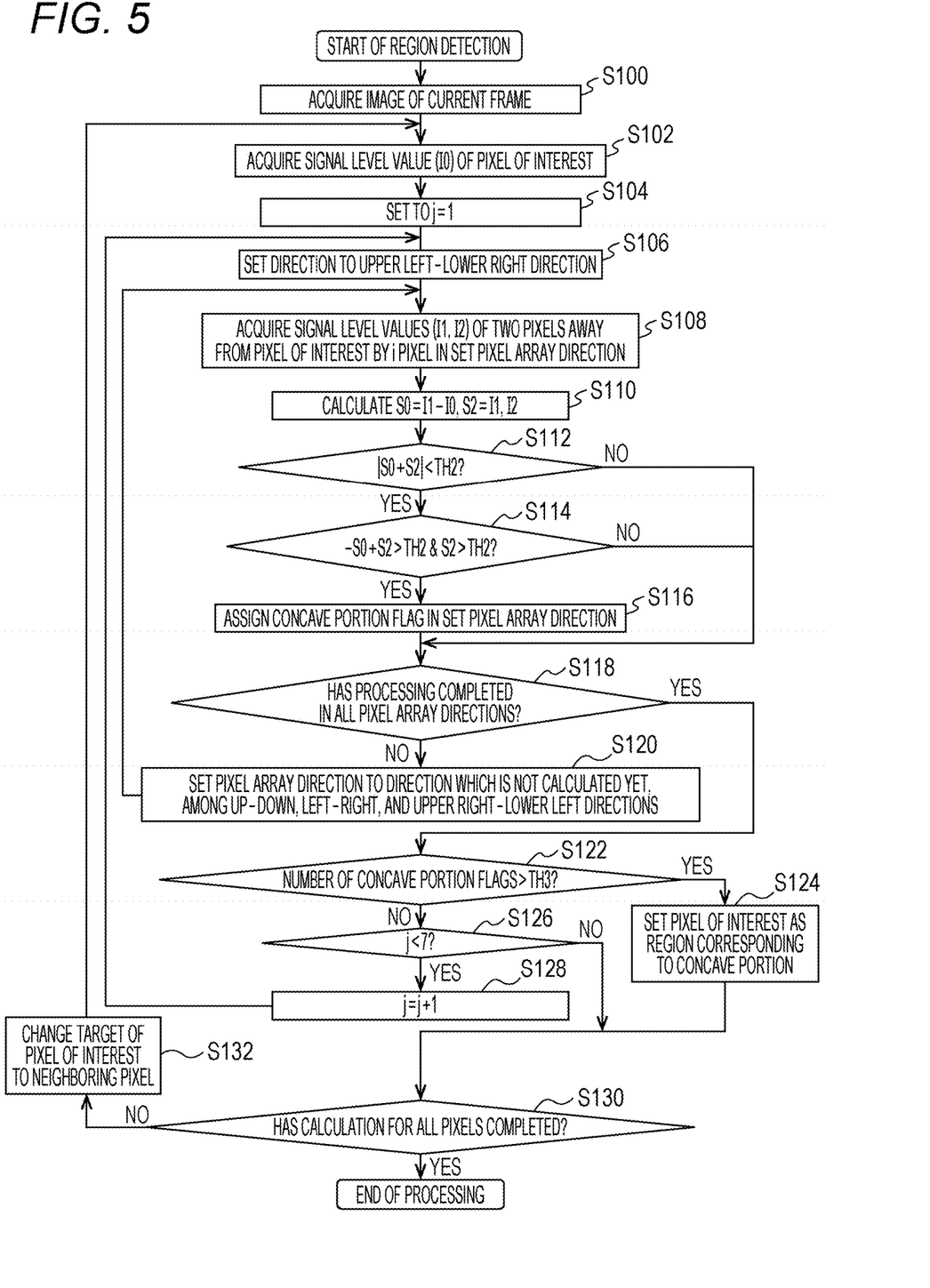
FIG. 5 is a flowchart illustrating an example of a flow of a region detection processing of an embodiment performed by an electronic endoscope system.

FIG. 5 is a flowchart illustrating an example of a flow of the region detection processing according to the embodiment, which is performed by the region detection unit 30.

The region detection unit 30 calls a captured image of a current frame captured by the electronic scope 100 and stored in the image memory 27 via the system controller 21 to acquire the captured image (Step S100).

Next, the region detection unit 30 defines a pixel of interest, and acquires a signal level value of this pixel (Step S102). It is assumed that the signal level value of the pixel of interest is I0.

Next, the region detection unit 30 sets a variable j to one and selects a frame of $(2 \cdot j+1) \times (2 \cdot j+1)$ pixels (Step S104).

The region detection unit 30 disposes the selected frame on the captured image such that a center pixel of the selected frame matches the pixel of interest, and sets the pixel array direction for the pixel of interest to the upper left-lower right direction (Step S106). The region detection unit 30 acquires signal level values of two farthest pixels located on both sides in the frame in the set pixel array direction from the pixel of interest (Step S108). At this time, the signal level values of two farthest pixels are defined as I1 and I2.

The region detection unit 30 calculates I1−I0 and I2−I1, and sets difference results to S0 and S2, respectively (Step S110).

Next, the region detection unit 30 determines whether or not a result of calculating an absolute value of S0+S2 is less than a predetermined threshold TH2 (Step S112). Here, the absolute value of S0+S2 is an absolute value of a difference between the signal level values of two farthest pixels, which indicates that it is determined whether or not the absolute value of the difference between the signal level values of two farthest pixels is less than the threshold TH2. When it is determined to be negative (No), the region detection unit 30 determines that the pixel of interest is not a candidate for the enhancement processing target region in the set pixel array direction, and causes the processing to proceed to Step S118 which will be described later. On the other hand, when it is determined to be affirmative (Yes), the region detection unit 30 determines whether or not −S0 and S2 are larger than a threshold TH1 (Step S114). When it is determined to be negative (No), the region detection unit 30 determines that the pixel of interest is not a candidate for the enhancement processing target region in the defined pixel array direction, and causes the processing to proceed to Step S118 which will be described later. On the other hand, when the it is determined to be affirmative (Yes) in Step S114, the region detection unit 30 determines that the pixel of interest is the candidate for the enhancement processing target region (candidate for a region corresponding to the concave portion) in the set pixel array direction, and assigns a concave portion flag to a pixel information recording region set for each pixel array direction corresponding to the pixel of interest (Step S116).

Next, the region detection unit 30 determines whether or not Steps S108 to S118 have been executed for all the pixels in the pixel array direction (Step S118). In a case where it is determined to be negative (No), the region detection unit 30 sets the pixel array direction in which the processing of Steps S108 to S118 are performed to one pixel array direction that is not set (Step S120). In this manner, the processing of Steps S108 to 118 are repeated while changing the pixel array direction until it is determined to be affirmative (Yes) in Step S118. In a case where it is determined to be affirmative (Yes) in Step S118, the region detection unit 30 determines whether or not the number of times the concave portion flag has been given in the current pixel of interest exceeds a set threshold count TH3 (Step S122). In a case where it is determined to be affirmative, the region detection unit 30 sets the pixel of interest as the enhancement processing target region (region corresponding to the concave portion) (Step S124). Thereafter, the processing proceeds to Step S130 which will be described later in order to change the pixel of interest. The threshold count TH3 may be one, but is preferably two or more in order to increase the extraction accuracy for the region corresponding to the concave portion.

In a case where it is determined to be negative (No) in Step S122, it is determined whether or not the set variable j is less than seven, that is, whether or not all the frames of (2·j+1)×(2·j+1) pixels smaller than the frame of 15×15 pixels are selected (Step S126). In a case where it is determined to be affirmative (Yes), the region detection unit 30 increases the variable j by one (Step S128), that is, increases the frame size, and returns the processing to Step S106. Thus, the region detection unit 30 repeats Steps S106 to S124 while gradually increasing the frame size until it is determined to be affirmative (Yes) in Step S126.

In a case where it is determined to be negative (No) in Step S126 or in a case where the pixel of interest is set as the enhancement processing target region (region corresponding to the concave portion) in Step S124, the region detection unit 30 determines whether or not the calculation of the above-described processing has been completed with all the pixels of the captured image as the pixel of interest (Step S130). In a case where it is determined to be negative (No), the region detection unit 130 changes the target of the pixel of interest to a neighboring pixel and sets the neighboring pixel as a pixel of interest (Step S132). In a case where it is determined to be affirmative (Yes) in Step S130, the region detection unit 130 ends the region detection processing. In this manner, the processing of Steps S102 to S132 are repeated until the region detection processing is performed on all the pixels of the captured image.

In this manner, in a case where the signal level value of the pixel of interest is smaller than the signal level values of two farthest pixels in any one of a plurality of pixel array directions in the region surrounded by the frame surrounding the region centered on the pixel of interest in the captured image, the region detection unit 30 is configured to repeat the candidate extraction processing of extracting the pixel of interest as the candidate for the enhancement processing target region while changing the size of the frame and to define the enhancement processing target region based on the candidate pixels extracted as the candidates by changing the size. Here, the candidate extraction processing corresponds to processing of Steps S108 to S120 in the example of the flow illustrated in FIG. 5. Thus, it is possible to increase the concave portion extraction accuracy with respect to various sizes of concave portions in the captured image. Furthermore, even when the resolution of the captured image (distance on the object corresponding to a length of one side of each pixel) is different, the concave portion in the captured image can be reliably extracted. Therefore, it is possible to perform the enhancement processing on a larger number of concave portions than those of the related art.

Although a total of six types of fames from the minimum-size frame of 3×3 pixels to the frame size of 13×13 pixels have been used in the frame sizes in the flow illustrated in FIG. 5, the frame size to be used and the number of frames to be used are not particularly limited.

Next, the enhancement processing unit 31 will be described.

The enhancement processing unit 31 performs enhancement processing on each pixel of the enhancement processing target region set as a region corresponding to the concave portion by the processing of the region detection unit 30.

Figure 6:
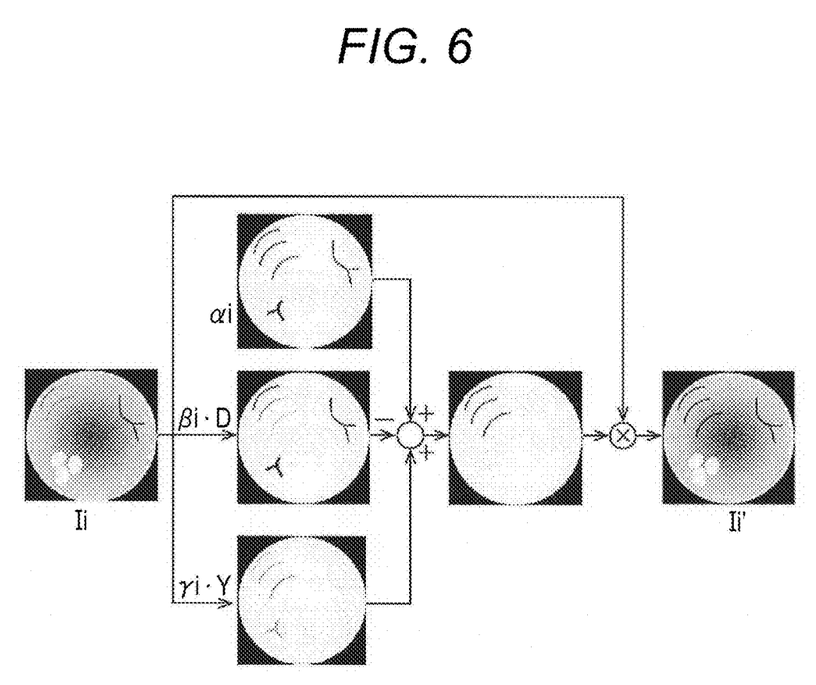
FIG. 6 is a block diagram illustrating a principle of enhancement processing of an embodiment.

FIG. 6 is a block diagram illustrating a principle of enhancement processing of the embodiment. FIG. 6 illustrates a change after the processing corresponding to each term of the right side of Equation (1) is performed on the captured image of the living tissue. In the example of the captured image illustrated in FIG. 6, there is a concave portion at the center, and a blood vessel and a highlight portion are included around the concave portion.

In the image obtained after the enhancement processing, it can be seen that enhancement of surrounding blood vessels or the like can be suppressed while enhancing the concave portion at the center of the image before the enhancement processing.

Figure 7:
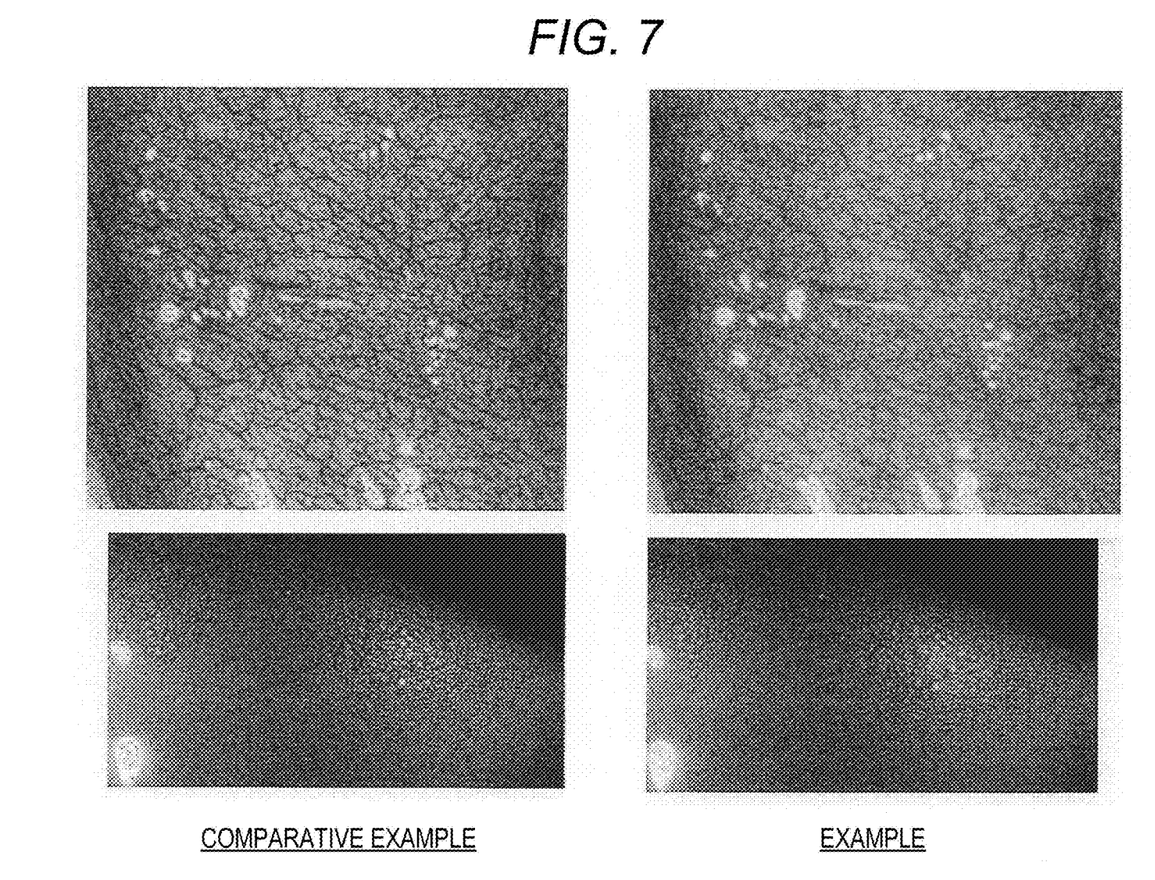
FIG. 7 is a view illustrating images of an affected portion before and after enhancement processing is performed.

FIG. 7 illustrates an image obtained by enhancement processing of the related art as a comparative example and the enhancement processing of the embodiment performed according to Equation (1) as an example. Note that the enhancement processing of the related art indicates a case where the enhancement processing is performed such that the enhancement is strengthened as the depth information D is larger.

As illustrated in FIG. 7, in the enhancement processing of the related art, which is illustrated as the comparative example, it can be seen that the blood vessel is unnaturally enhanced, whereas in the example, the enhancement of the blood vessel and the enhancement of the highlight portion are weakened, and the concave portion is easily recognized. In other words, in the enhancement processing of the present embodiment illustrated in the example of FIG. 7, it can be seen that a state in which the pigmentation is performed can be reproduced in a pseudo manner.

Figure 8:
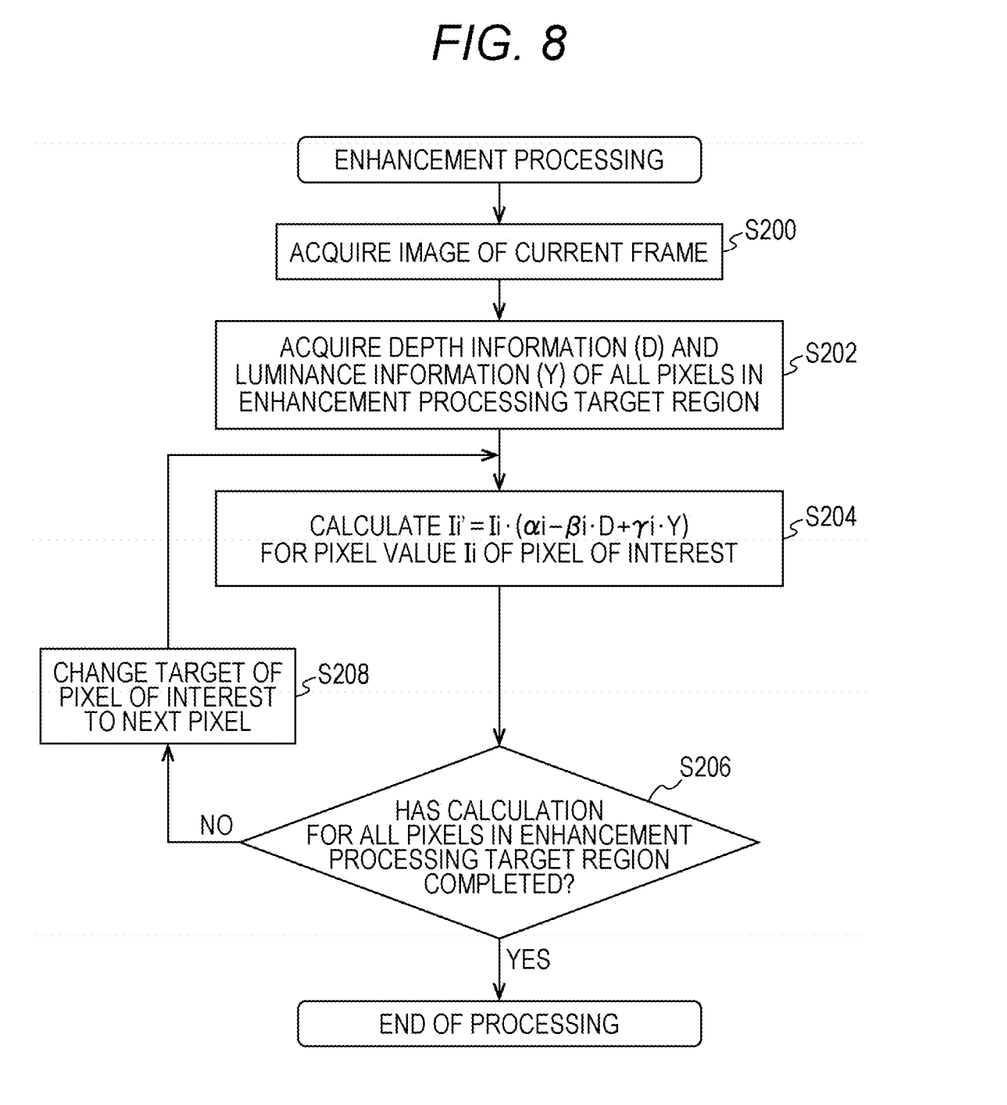
FIG. 8 is a flowchart illustrating an example of a flow of an enhancement processing of an embodiment performed by an electronic endoscope system.

FIG. 8 is a flowchart illustrating an example of a flow of the enhancement processing according to the embodiment, which is performed by the enhancement processing unit 31.

With reference to FIG. 8, the enhancement processing unit 31 first calls a captured image of a current frame captured by the electronic scope 100 and stored in the image memory 27 via the system controller 21 to acquire the captured image (Step S200).

Next, the enhancement processing unit 31 acquires depth information (D) and luminance information (Y) of each of all pixels in the enhancement processing target region (region corresponding to the concave portion) set by the region detection unit 30 from the captured image acquired in Step S200 (Step S202). The enhancement processing unit 31 sequentially defines each pixel in the enhancement processing target region (region corresponding to the concave portion) as a pixel of interest, and sequentially executes processing of step S204 until the calculation for all the pixels in the enhancement processing target region is completed (Steps S206 and S208).

In Step S204, the enhancement processing unit 31 performs the calculation of Equation (1) (that is, $Ii'=Ii \cdot (\alpha i - \beta i \cdot D + \gamma i\, Y)$) on the pixel value Ii of the pixel of interest i and calculates the pixel value Ii' after the enhancement processing. When the processing of Step S204 ends for all the pixels in the enhancement processing target region, the enhancement processing ends (Step S206: YES).

As described above, according to the processor 200 of the electronic endoscope system of the embodiment, the enhancement processing target region (region corresponding to the concave portion), in which the enhancement processing of the captured image is to be performed, is detected, and then the enhancement processing is performed on each pixel of the enhancement processing target region. At this time, the enhancement processing is performed such that the enhancement is weakened as the signal level difference is larger, and the enhancement is strengthened as the luminance is higher. Therefore, in the captured image, by enhancing the concave portion of the mucous membrane without performing great enhancement on a portion that is not a concave portion and has a large signal level difference from the vicinity, such as a blood vessel or a highlight portion, it is possible to more effectively make the lesion noticeable.

As described above, in Equation (1) when the enhancement processing is performed, the enhancement coefficients $\alpha i$, $\beta i$, and $\gamma i$ may be individually set for each of the RGB components of the pixel included in the enhancement processing target region. By configuring to be individually settable for each color component, the color balance of the concave portion can be varied, and the state in which the pigmentation is performed on the lesion can be reproduced in a pseudo manner.

Furthermore, the processor 200 of the electronic endoscope system of the embodiment may further include an input unit for setting or changing the enhancement coefficients $\alpha i$, $\beta i$, and $\gamma i$. For example, the processor may include an input interface for receiving input of setting change of the enhancement coefficients $\alpha i$, $\beta i$, and $\gamma i$ through the operation panel 24. Therefore, the observer of the lesion of the patient can set the image in which the lesion is easily observed in real time.

In Equation (1), a case where the luminance information (Y) is multiplied by the enhancement coefficient $\gamma i$ in order to perform the enhancement processing such that the enhancement is strengthened as the luminance is higher has been described, but the present invention is not limited thereto. Since it is only necessary to enhance a portion of higher luminance, a value of an R component and/or a G component may be used instead of the luminance information (Y) in Equation (1). That is, the enhancement processing may be performed on the pixel value of each pixel of interest such that the larger the value of the R component and/or the G component, the larger the pixel value after the enhancement processing.

Although the processor for an electronic endoscope and the electronic endoscope system of the present invention has been described in detail as described above, the processor for an electronic endoscope and the electronic endoscope system of the present invention are not limited to the above-described embodiment, and may, of course, be modified or altered in various ways in a range not deviating from the spirit of the present invention.

The present invention relates to a patent application of Japanese Patent Application No. 2021-060673 filed with the Japan Patent Office on Mar. 31, 2021, the entire contents of which are incorporated herein by reference.

The invention claimed is:

1. A processor for an electronic endoscope that acquires a captured image of a living tissue and performs enhancement processing, the processor comprising:
   a region detection unit configured to detect an enhancement processing target region in the captured image of the living tissue from pixel information of the captured image; and
   an enhancement processing unit configured to perform enhancement processing on the enhancement processing target region detected by the region detection unit,
   wherein the region detection unit detects the enhancement processing target region based on a difference in signal level between a pixel of interest in the captured image and a pixel surrounding the pixel of interest, and
   the enhancement processing unit performs the enhancement processing on the enhancement processing target region such that:
      enhancement is weakened as the difference in signal level between the pixel of interest in the captured image and the pixel surrounding the pixel of interest is larger, and
      the enhancement is strengthened as luminance is higher.

2. The processor for an electronic endoscope according to claim 1, wherein the enhancement processing is processing of correcting a pixel value of a pixel included in the enhancement processing target region based on a first coefficient for the difference in signal level and a second coefficient for intensity of the luminance.

3. The processor for an electronic endoscope according to claim 2,
wherein the first coefficient and/or the second coefficient are individually set for each of RGB components of the pixel included in the enhancement processing target region.

4. The processor for an electronic endoscope according to claim 2,
further comprising an input unit for setting or changing the first coefficient and the second coefficient.

5. The processor for an electronic endoscope according to claim 1,
wherein the enhancement processing is performed such that the enhancement is strengthened as a value of an R component and/or a value of a G component of a pixel included in the enhancement processing target region is larger.

6. The processor for an electronic endoscope according to claim 1,
wherein, in a case where a signal level value of the pixel of interest is smaller than signal level values of two farthest pixels located on both sides farthest from the pixel of interest in any one of a plurality of pixel array directions in a region surrounded by a frame surrounding a region centered on the pixel of interest, the region detection unit is configured to repeat candidate extraction processing of extracting the pixel of interest as a candidate for the enhancement processing target region while changing a size of the frame and to define the enhancement processing target region based on the pixel extracted as the candidate by changing the size of the frame.

7. An electronic endoscope system comprising:
the processor for an electronic endoscope according to claim 1; and
an electronic endoscope that is connected to the processor for an electronic endoscope and includes an image sensor configured to capture the living tissue.

8. The processor for an electronic endoscope according to claim 1, wherein the pixel of interest at the time of detecting an enhancement processing target region is a center pixel.

9. The processor for an electronic endoscope according to claim 1, wherein the pixel of interest is a candidate for the enhancement processing target region.

\* \* \* \* \*